United States Patent [19]
Winklter et al.

[11] Patent Number: 6,025,502
[45] Date of Patent: Feb. 15, 2000

[54] ENANTOPSELECTIVE SYNTHESIS OF METHYL PHENIDATE

[75] Inventors: Jeffrey David Winklter, Wynnewood; Jeffrey M. Axten; Lori Krim, both of Philadelphia, all of Pa.

[73] Assignee: The Trustees of the University of Pennsylvania, Philadelphia, Pa.

[21] Appl. No.: 09/273,144

[22] Filed: Mar. 19, 1999

[51] Int. Cl.$^7$ .................................................. C07D 211/08
[52] U.S. Cl. .................................................................. 549/21
[58] Field of Search ............................ 514/330; 546/225, 546/226, 227, 228, 192

[56] References Cited

U.S. PATENT DOCUMENTS

| | | | |
|---|---|---|---|
| 2,507,631 | 5/1950 | Hartmann et al. | 546/192 |
| 2,835,519 | 5/1958 | Spicacci . | |
| 2,838,519 | 6/1958 | Rometsch | 546/192 |
| 2,957,880 | 10/1960 | Rometsch et al. | 546/227 |
| 4,160,452 | 7/1979 | Theeuwes . | |
| 4,256,108 | 3/1981 | Theeuwes . | |
| 4,265,874 | 5/1981 | Bonsen et al. . | |
| 5,859,249 | 1/1999 | Seido et al. | 546/235 |
| 5,908,850 | 6/1999 | Zeitlin et al. | 514/315 |

FOREIGN PATENT DOCUMENTS

| | | |
|---|---|---|
| 788226 | 12/1957 | United Kingdom . |
| 878167 | 9/1961 | United Kingdom . |
| 466229 | 12/1975 | United Kingdom . |
| 97-27176 | 7/1997 | WIPO . |
| WO97/27176 | 7/1997 | WIPO . |
| WO97/28124 | 8/1997 | WIPO . |
| WO97/35836 | 10/1997 | WIPO . |
| 98/25902 | 6/1998 | WIPO . |
| WO98/25902 | 6/1998 | WIPO . |

OTHER PUBLICATIONS

Deutsch et al., 1996, J. Med. Chem. 39:1201–1209.
Doyle et al., 1995, Recl. Trav. Chim. Pays–Bas 114:163–170.
Earle et al., 1969, J. Chem. Soc. C:2093–2098.
Naito et al., 1964, Chem. Pharm. Bull. 12:588–590.
Padmanabhan, 1981, *Analytical Profiles of Drug Substances,* v. 10, Florey, Ed., Academica Press, New York.
Panizzon, 1944, Helv. Chim. Acta 27:1748–1756.
Patrick et al., 1987, J. Pharmacol. Exp. Therapeut. 241:152–158.

*Primary Examiner*—Deborah C. Lambkin
*Attorney, Agent, or Firm*—Akin, Gump, Strauss, Hauer & Feld, L.L.P.

[57] ABSTRACT

The invention relates to an enantioselective method of making methylphenidate and derivatives thereof. The method involves use of a rhodium catalyst, and selectively produces the D-enantiomer of the methylphenidate derivative in excess of the L-enantiomer thereof. Furthermore, the method selectively produces the threo-diastereomer in excess of the erythro-diastereomer. The method is thus suitable for synthesis of D-threo-methylphenidate (the biologically active form of this compound) and derivatives thereof.

17 Claims, 1 Drawing Sheet

ENANTOPSELECTIVE SYNTHESIS OF METHYL PHENIDATE

STATEMENT REGARDING FEDERALLY SUPPORTED RESEARCH AND DEVELOPMENT

This research was supported in part by U.S. Government finds (NIH grant number CA 40250), and the U.S. Government may therefore have certain rights in the invention.

FIELD OF THE INVENTION

The field of the invention is synthesis of methylphenidate and derivatives thereof.

BACKGROUND OF THE INVENTION

Methylphenidate (Ritalin,™ Ciba-Geigy Corporation, Summit, N.J.) is the most commonly prescribed psychotropic medication for children in the United States. It is used primarily for the treatment of children diagnosed with attention deficit disorder (ADD). Methylphenidate is synonymous with methyl α-phenyl-2-piperidineacetate, α-phenyl-2-piperidineacetate methyl ester, methyl phenidylacetate, and methylphenidan. The biologically active form of methylphenidate is the D-threo enantiomer. Methylphenidate is sold, in the form of the hydrochloride salt, as the product Ritalin™ and its generic equivalents. A comprehensive description of the compound is found in Padmanabhan (1981, *Analytical Profiles of Drug Substances* v. 10, Florey, Ed., Academic Press, New York).

D-threo-methylphenidate is a mild central nervous system stimulant. Its mode of action in humans is not fully understood, but presumably involves activation of the brain stem arousal system to effect stimulation of the patient. Dosing and administration information, contraindications, warnings, and precautions pertaining to administration of methylphenidate to humans is available in the art (e.g. Physician's Desk Reference®, Medical Economics Co., Inc., Montvale, N.J., 51st ed., 1997; PDR® Generics™, Medical Economics Co., Inc., Montvale, N.J., 2nd ed., 1996). Methylphenidate is the treatment of choice for attention deficit disorder, and is also used in the treatment of narcolepsy, minimal cerebral dysfunction, and other conditions. In addition, methylphenidate and its analogs have been proposed as cocaine antagonists for treatment of cocaine abuse and addiction (e.g. International Patent Application PCT/US99/00711 and Deutsch et al., 1996, J. Med. Chem. 39:1201–1209).

Numerous methods for synthesizing methylphenidate, for interconverting the diastereomers of methylphenidate, and for resolving the enantiomers of methylphenidate have been described in the art (U.S. Pat. No. 2,507,631 to Hartmann; U.S. Pat. No. 2,838,519 to Rometsch; U.S. Pat. No. 2,957,880 to Rometsch; British Patent Nos. 788,226 and 878,167, each to Ciba Ltd.; Soviet Patent No. 466,229 to Yakhontov et al.; International Patent Application Publication No. WO9735836 of Fox et al.; International Patent Application Publication No. WO9728124 of Langston et al.; Panizzon, 1944, Helv. Chim. Acta 27:1748–1756; Naito et al., 1964, Chem. Pharm. Bull. 12:588–590; Deutsch et al., 1996, J. Med. Chem. 39:1201–1209; Earle et al., 1969, J. Chem. Soc. (C) 2093–2098; International Patent Application Publication No. WO9825902 of Faulconbridge et al.; Patrick et al., 1987, J. Pharmacol. Exp. Therapeut. 241:152–158 International Patent Application Publication No. WO9727176 of Harris et al.; International Patent Application Publication No. WO9825902 of Zavareh. These methods have various shortcomings, including low yield, the necessity to interconvert diastereomers of methylphenidate following synthesis, and the necessity to resolve enantiomers of methylphenidate. Furthermore, investigation of methylphenidate analogs has been hampered by the fact that these methods can be used to synthesize only a narrow range of analogs, such as methylphenidate analogs having ester modifications or phenyl ring substitutions.

The present invention overcomes the shortcomings of these synthetic methods, and provides D-threo-methylphenidate and numerous D-threo-methylphenidate derivatives, including efficacious cocaine antagonists and analogs useful for treatment of various neurological disorders.

BRIEF SUMMARY OF THE INVENTION

The invention relates to a method of synthesizing a methylphenidate derivative having the formula (I)

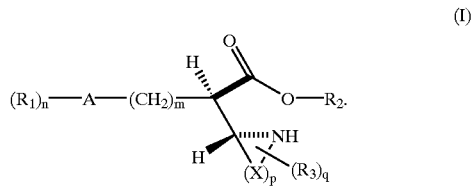

The method comprises
(a) combining, in the presence of a rhodium catalyst, a first compound having the formula (II) and a second compound having the formula (III) and thereafter removing the nitrogen-protecting group of formula (III), whereby the compound having the formula (I) is generated. Formula (II) is

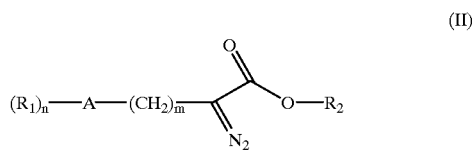

wherein
n is an integer selected from the group consisting of the integers from 0 to 7;
$R_1$ is independently selected from the group consisting of cycloaryl, $C_1$–$C_6$ alkyl, $C_1$–$C_6$ alkoxy, hydroxyl, $C_1$–$C_6$ alkanoyl, halogen, amino, $C_1$–$C_6$ alkylamino, nitro, sulfo, and sulfhydryl;
A is selected from the group consisting of a cycloaryl group and a fused cycloaryl group;
m is an integer selected from the group consisting of 0 and 1; and
$R_2$ is selected from the group consisting $C_1$–$C_6$ alkyl and $C_1$–$C_6$ alkanoyl. Formula (III) is

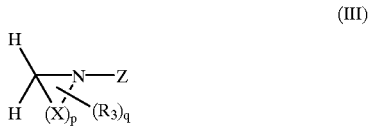

wherein
- p is an integer selected from the group consisting of 3, 4, 5, and 6;
- X is an atom independently selected from the group consisting of carbon, oxygen, nitrogen, and sulfur;
- q is an integer selected from the group consisting of the integers from 0 to 16;
- $R_3$ is independently selected from the group consisting of hydrogen, $C_1$–$C_6$ alkyl, $C_1$–$C_6$ alkoxy, hydroxyl, $C_1$–$C_6$ alkanoyl, halogen, carboxyl, $C_2$–$C_6$ alkanoxy, nitro, sulfo, and sulfhydryl, or wherein two of $R_3$ are, together, an oxo group or a double bond between two adjacent X atoms; and
- Z is a nitrogen-protecting group.

The nitrogen-protecting group may, for example, be selected from the group consisting of a 9-fluorenylmethoxy-carbonyl group, and a butoxycarbonyl group, and is preferably the latter. The rhodium catalyst may, for example, be a dirhodium (II) tetrakis[methyl 2-oxopyrrolidine-5(R)-carboxylate] catalyst.

In one aspect of this method, one or more of the following conditions is satisfied:
a) each X is carbon;
b) p is 4;
c) q is 8 and each $R_3$ is hydrogen; and
d) A is a phenyl group.

In another aspect of this method, one or more of the following conditions is satisfied:
a) n is 0;
b) A is a phenyl group; and
c) m is 0.

$R_2$ is preferably methyl.

In yet another aspect of this method, the methylphenidate derivative is D-threo-methylphenidate. For example, the first compound may be methylphenyl-diazoacetate, and the second compound may be N-butoxycarbonyl piperidine.

Preferably, according to this method, the ratio of the methylphenidate derivative to the erythro-diastereomer thereof is greater than 1.00. Also preferably, the ratio of the methylphenidate derivative to the L-enantiomer thereof is greater than 1.00.

The invention also includes a methylphenidate derivative having the formula (I)

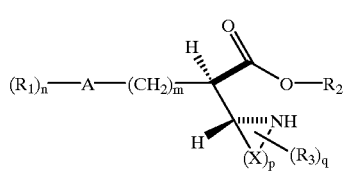

(I)

wherein the methylphenidate derivative is made by the method of the invention.

The invention further includes a pharmaceutical composition comprising the methylphenidate derivative of the invention and a pharmaceutically acceptable carrier. The methylphenidate derivative is preferably D-threo-methylphenidate.

DETAILED DESCRIPTION

Figure 1:
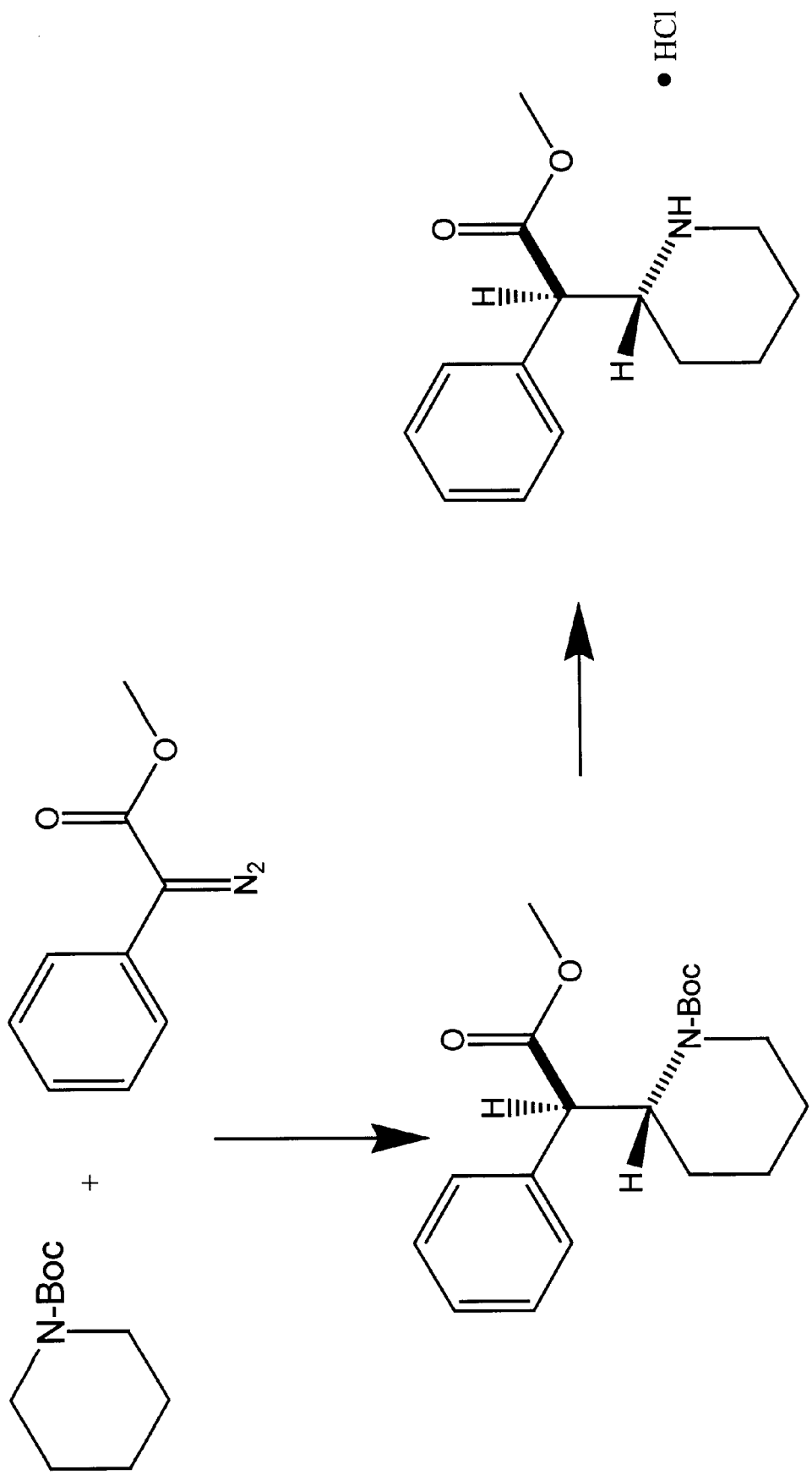
FIG. 1 is an outline of the synthetic method employed in Example 1 for synthesis of D-threo-methylphenidate.

The invention relates to an enantioselective method of synthesizing methylphenidate and derivatives thereof. Prior art methods of synthesizing such compounds yield a racemic mixture of the D- and L-enantiomers. It is known that the D-enantiomer of compounds such as methylphenidate (particularly D-threo-methylphenidate) exhibit greater biological activities than the corresponding L-enantiomers.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

A "derivative" of methylphenidate means a compound (including methylphenidate) having the chemical structure,

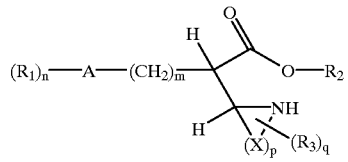

wherein
- n is an integer selected from the group consisting of the integers from 0 to 7;
- $R_1$ is independently selected from the group consisting of cycloaryl, $C_1$–$C_6$ alky, $C_1$–$C_6$ alkoxy, hydroxyl, $C_1$–$C_6$ alkanoyl, halogen, amino, $C_1$–$C_6$ alkylamino, nitro, sulfo, and sulfhydryl;
- A is selected from the group consisting of a cycloaryl group and a fused cycloaryl group;
- m is an integer selected from the group consisting of 0 and 1;
- $R_2$ is selected from the group consisting $C_1$–$C_6$ alkyl and $C_1$–$C_6$ alkanoyl;
- p is an integer selected from the group consisting of 3, 4, 5, and 6;
- X is an atom independently selected from the group consisting of carbon, oxygen, nitrogen, and sulfur;
- q is an integer selected from the group consisting of the integers from 0 to 16; and
- $R_3$ is independently selected from the group consisting of hydrogen, $C_1$–$C_6$ alky, $C_1$–$C_6$ alkoxy, hydroxyl, $C_1$–$C_6$ alkanoyl, halogen, carboxyl, $C_2$–$C_6$ alkanoxy, nitro, sulfo, and sulfhydryl, or wherein two of $R_3$ are, together, an oxo group or a double bond between two adjacent X atoms.

As used herein, "D-threo-methylphenidate" means the compound having the following formula.

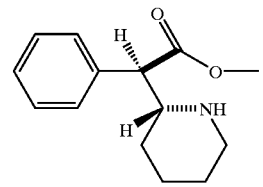

A "fused cycloaryl group" is a chemical moiety comprising two or more cycloaryl moieties in which at least two of the cycloaryl moieties have at least two atoms in common. Examples of a fused cycloaryl groups include a naphthyl moiety (which comprises two fused phenyl moieties), a phenanthrene moiety, and an anthracene moiety.

Description

The invention includes an enantioselective method of synthesizing a methylphenidate derivative having the formula (I)

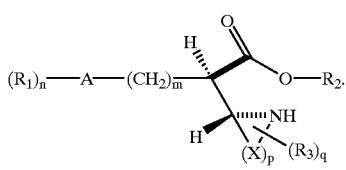

(I)

The method of the invention comprises combining a compound (herein designated "a first compound") having the formula (II) and a compound (herein designated "a second compound") having the formula (III) in the presence of a rhodium catalyst to form a reaction intermediate, and thereafter removing the nitrogen-protecting group (i.e. Z in formula {III}) from the reaction intermediate. The catalyst is preferably a dirhodium (II) tetrakis[methyl 2-oxopyrrolidine-5(R)-carboxylate] (herein "$Rh_2\{5R\text{-}MBPY\}_4$") catalyst.

Formula (II) is

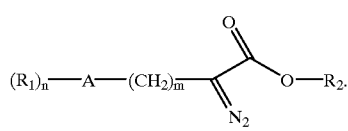

(II)

In formula (II),
n is an integer selected from the group consisting of the integers from 0 to 7;
$R_1$ is independently selected from the group consisting of cycloaryl, $C_1$–$C_6$ alkyl $C_1$–$C_6$ alkoxy, hydroxyl, $C_1$–$C_6$ alkanoyl, halogen, amino, $C_1$ –$C_6$ alkylamino, nitro, sulfo, and sulfhydryl;
A is selected from the group consisting of a cycloaryl group and a fused cycloaryl group;
m is an integer selected from the group consisting of 0 and 1; and
$R_2$ is selected from the group consisting $C_1$–$C_6$ alkyl and $C_1$–$C_6$ alkanoyl.

In formula (II), each $R_1$ is independently selected. Thus, the fused cycloaryl group may have more than one type of substituent (e.g. both hydrogen atoms and halogen atoms). Preferred first compounds include, for example, methyl phenyldiazoacetate, ethyl phenyldiazoacetate, methyl 1-naphthyldiazoacetate, and ethyl 1-naphthyldiazoacetate.

Formula (III) is

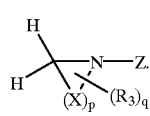

(III)

In Formula (III),
p is an integer selected from the group consisting of 3, 4, 5, and 6;

X is an atom independently selected from the group consisting of carbon, oxygen, nitrogen, and sulfur;
q is an integer selected from the group consisting of the integers from 0 to 16; and
$R_3$ is independently selected from the group consisting of hydrogen, $C_1$–$C_6$ alkyl, $C_1$–$C_6$ alkoxy, hydroxyl, $C_1$–$C_6$ alkanoyl, halogen, carboxyl, $C_2$–$C_6$ alkanoxy, nitro, sulfo, and sulfhydryl, or wherein two of $R_3$ are, together, an oxo group or a double bond between two adjacent X atoms; and
Z is a nitrogen-protecting group.

Each X in formula (III) is preferably carbon, although heterocyclic rings comprising more than the nitrogen atom indicated in formula (III) may also be used. Non-aryl compounds having formula (III) are preferred in the methods of the invention. The nitrogen-protecting group may be any of a wide variety of nitrogen-protecting groups such as, for example, a butoxycarbonyl ("Boc") group, a 9-fluorenylmethoxy-carbonyl ("Fmoc") group, and the like. Methods of removing nitrogen-protecting groups are well known in the art. By way of example, it is known that Boc groups are acid labile, and may be removed by treatment with trifluoroacetic acid, and that Fmoc groups are base labile, and may be removed by treatment with piperidine. Suitable second compounds include, for example, N-Boc-piperidine, N-Boc-pyrrolidine, and N-Boc-pyridine.

Combining the first and second compounds in the presence of a rhodium catalyst leads to formation of a reaction intermediate having the following formula, in which the ratio of the D-enantiomer to the L-enantiomer is greater than 1.00, and is preferably greater than about 1.25 or 1.5, and in which the ratio of the ratio of the threo-diastereomer to the erythro-diastereomer is greater than 1.00, and is preferably greater than about 2, 5, or 10.

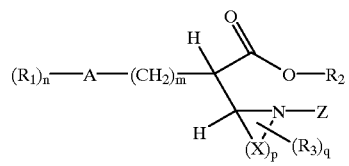

Removal of the nitrogen-protecting (i.e. Z) group from this intermediated yields the methylphenidate derivative having the enantiomeric and diastereomeric ratios described above. When the nitrogen-protecting group is a Boc group, for example, it may be removed by maintaining the reaction intermediate in an acidic environment (e.g. in HCl-acidified methanol at 0° C.).

As noted above, prior art methods of making methylphenidate were not enantioselective (as are the methods of the invention), and yielded a racemic mixture of enantiomers. Thus, prior art methods of methylphenidate synthesis require post-synthetic processing to resolve the enantiomers. Furthermore, most prior art synthetic methods also required resolution of the diastereomers of methylphenidate. While these prior art post-synthetic processing methods may, of course, be used to further improve the enantiomer and/or diastereomer content of the product, such processing is not necessary according to the methods of the invention, because the product of the methods of the invention is enriched for both the threo- diastereomer (e.g. 94% or more of the product) and the D-enantiomer (e.g. 69% or more of the product). Thus, at least about 63% of the product of the synthetic method of the invention is the D-threo- form of the methylphenidate derivative. In contrast, only 25% of the product would be expected to be in the D-threo- form if the enantiomers and diastereomers produced in the reaction were random.

The invention also includes methylphenidate derivatives made by the methods of the invention. Such derivatives have the formula (I)

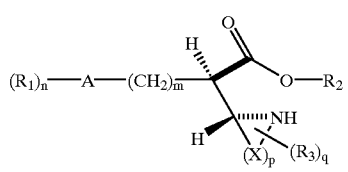

wherein the designations are as previously described herein. The ratios of enantiomers and diastereomers of these derivatives are preferably as described elsewhere herein. The derivatives may be prepared in the form of a salt (e.g. a hydrochloride or an acetate salt) or in the free-base form, using methods well known in the art.

Pharmaceutical Compositions

The invention encompasses preparation and use of medicaments and pharmaceutical compositions comprising one or more of the methylphenidate derivatives of the invention as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. Administration of one of these pharmaceutical compositions to a subject is useful for treating a variety of conditions such as attention deficit disorder, cocaine abuse, and cocaine addiction in the subject. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject As used herein, the term "physiologically acceptable" ester or salt means an ester or salt form of the active ingredient which is compatible with any other ingredients of the pharmaceutical composition and which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, although the compositions should also be efficacious in other mammals.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient. A unit dose of a pharmaceutical composition of the invention will generally comprise from about 1 nanogram to about 5 grams of the active ingredient, and preferably comprises from about 1 milligram to about 500 milligrams of the active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para- hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intravenous, intraarterial, intramuscular, or intrastemal injection and intravenous, intraarterial, or kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

A pharmaceutical composition of the invention may be administered to deliver a dose of between 1 ng/kg/day and 100 mg/kg/day, and preferably to deliver of between 50 ng/kg/day and 10 mg/kg/day, to a subject.

It is understood that the ordinarily skilled physician or veterinarian will readily determine and prescribe an effective amount of the compound to treat ADD, cocaine addiction, or another disease or disorder for which dopamine re-uptake inhibitors such as methylphenidate derivatives are known or believed to be efficacious. In so proceeding, the physician or veterinarian may, for example, prescribe a relatively low dose at first, subsequently increasing the dose until an appropriate response is obtained. It is further understood, however, that the specific dose level for any particular subject will depend upon a variety of factors including the activity of the specific compound employed, the age, body weight, general health, gender, and diet of the subject, the time of administration, the route of administration, the rate of excretion, any drug combination, and the severity of the condition being treated.

Another aspect of the invention relates to a kit comprising a pharmaceutical composition of the invention and an instructional material. As used herein, an "instructional material" includes a publication, a recording, a diagram, or any other medium of expression which is used to communicate the usefulness of the pharmaceutical composition of the invention for treating ADD, cocaine addiction, or other conditions for which methylphenidate and derivatives thereof are known to be efficacious. The instructional material may also, for example, describe an appropriate dose of the pharmaceutical composition of the invention. The instructional material of the kit of the invention may, for example, be affixed to a container which contains a pharmaceutical composition of the invention or be shipped together with a container which contains the pharmaceutical composition. Alternatively, the instructional material may be shipped separately from the container with the intention that the instructional material and the pharmaceutical composition be used cooperatively by the recipient.

The invention also includes a kit comprising a pharmaceutical composition of the invention and a delivery device for delivering the composition to a subject. By way of example, the delivery device may be a squeezable spray bottle, a metered-dose spray bottle, an aerosol spray device, an atomizer, a dry powder delivery device, a self-propelling solvent/powder-dispensing device, a syringe, a needle, a tampon, or a dosage measuring container. The kit may further comprise an instructional material as described herein.

The invention is now described with reference to the following Example. This Example is provided for the purpose of illustration only, and the invention should in no way be construed as being limited to this Example, but rather should be construed to encompass any and all variations which become evident as a result of the teaching provided herein.

EXAMPLE 1

Synthesis of D-threo-methylphenidate

An enantioselective synthesis of a composition comprising D-threo-methylphenidate is described in this Example. This method yields a substantially greater proportion of the D- enantiomer of methylphenidate than non-enantioselective methods, and does not require chromatographic purification of this product from similar products in the reaction mixture. Furthermore, each of the synthetic steps is amenable to large-scale industrial chemical production methods and apparatus.

The synthetic method described in this Example is outlined in FIG. 1.

An oven-dried 5 milliliter flask containing a stirring bar was fitted with a septum and flame-dried while being purged with argon. 0.35 Milliliters of N-butoxycarbonyl piperidine ("Boc-piperidine") was added to the flask and degassed. An equal volume (i.e. 0.35 milliliters) of freshly distilled cyclohexane was then added to the flask. Next, 2.3 milligrams (2.51 millimoles) of $Rh_2\{5R\text{-}MEPY\}_4$ catalyst was added to the flask, and the reaction mixture was maintained at 50° C. for 20 minutes. Preparation of this catalyst is described, for example, by Doyle et al., 1995, Reel. Trav. Chim. Pays-Bas 114:163–170.

70.4 Milligrams (0.40 millimoles) of methyl phenyldiazoacetate was injected into the reaction mixture over the course of 4 hours. About 10 milligrams of the compound was be added at the beginning of the reaction and about every 30 minutes thereafter (the balance was added 30 minutes after the last 10 milligram addition). During this period, the reaction mixture was maintained at 50° C. and had a blue color. After this period, the reaction mixture was allowed to cool to room temperature (e.g. about 20° C.) over the course of about 30 minutes. The cooled reaction mixture was filtered at room temperature through a column containing a silica bed. The cylindrical silica bed had a diameter of about 5 millimeters and a height of about 100 millimeters. The silica column packing was flash silica. After the reaction mixture had been filtered through the silica column, the silica was washed with diethyl ether. The rhodium catalyst did not pass through the column, and therefore was not contained in the filtrate obtained from the silica column. This filtrate was concentrated in vacuo to yield a yellow oil. The yellow oil was purified by flash chromatography using a silica gel (EM Science; 244 mesh) column containing a bed having a diameter of 20 millimeters and a height of about 10 inches and a solution comprising 10% (v/v) diethyl ether and 90% petroleum ether (boiling point 30–60 C.). About 86 milligrams of boc-methylphenidate (i.e. ca. 64.5% yield) was obtained in the form of a green oil.

An oven-dried 15 milliliter flask containing a stirring bar was fitted with a septum, and 4.0 milliliters of methanol was added thereto. The methanol was cooled to 0° C., and HCl gas was bubbled through the cooled methanol for about 15 minutes. 2.2 milliliters of methanol was added to 206 milligrams (0.62 millimoles) of Boc-methylphenidate made as described above. This solution was added to the cooled acidified methanol solution, and this mixture was maintained at 0° C. for 30 minutes while stirring the mixture. The resulting liquid was concentrated in vacuo and triturated with ethyl acetate. The resulting white solid was washed with diethyl ether to yield 114.6 milligrams of the hydrochloride salt of D-threo-methylphenidate (i.e. 68.5% yield).

37.5 Milligrams (0.115 millimoles) of the salt was dissolved in 10 milliliters of a saturated solution of sodium bicarbonate, and then extracted twice with about 15 milliliters of diethyl ether to yield 30 milligrams of the free amine form of D-threo-methylphenidate (92% yield for the de-salting step).

The free amine form was applied to a Chiralcel ADTM analytical column (particle size ca. 10 micrometers) containing a bed having a diameter of about 4.6 millimeters and a length of 25 centimeters. The buffer applied to the column was a 98:2:0.1 mixture of hexane: isopropyl alcohol:diethyl alcohol, and the flow rate was 2.0 milliliters per minute. The retention times characteristic of the various enantiomers of methylphenidate under these column conditions are listed in Table 1.

TABLE 1

| Enantiomer of Methylphenidate | Characteristic Retention Time, minutes |
| --- | --- |
| l-erythro | 4.84 |
| d-erythro | 5.00 |
| l-threo | 6.61 |
| d-threo | 9.33 |

Chromatographic analysis of the free amine form of the reaction product indicated that at least 94% of the methylphenidate made using the methods described in this Example was the threo- diastereomer, and that at least 69% was the D-enantiomer. Thus, not less than about 63% of the methylphenidate made in this way was D-thieo-methylphenidate.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of synthesizing a methylphenidate derivative having the formula (I)

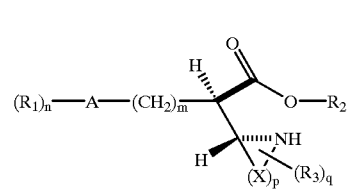

said method comprising
(a) combining, in the presence of a rhodium catalyst,
(i) a first compound having the formula (II)

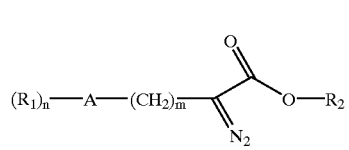

wherein n is an integer selected from the group consisting of the integers from 0 to 7;

wherein each $R_1$ is independently selected from the group consisting of cycloaryl, $C_1$–$C_6$ alkyl, $C_1$–$C_6$ alkoxy, hydroxyl, $C_1$–$C_6$ alkanoyl, halogen, amino, $C_1$–$C_6$ alkylamino, nitro, sulfo, and sulfhydryl;

wherein A is selected from the group consisting of a cycloaryl group and a fused cycloaryl group;

wherein m is an integer selected from the group consisting of 0 and 1; and wherein $R_2$ is selected from the group consisting $C_1$–$C_6$ alkyl and $C_1$–$C_6$ alkanoyl; and (ii) a second compound having the formula (III)

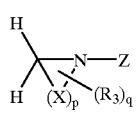

(III)

wherein p is an integer selected from the group consisting of 3, 4, 5, and 6;
wherein each X is an atom independently selected from the group consisting of carbon, oxygen, nitrogen, and sulfur,
wherein q is an integer selected from the group consisting of the integers from 0 to 16;
wherein each $R_3$ is independently selected from the group consisting of hydrogen, $C_1$–$C_6$ alkyl, $C_1$–$C_6$ alkoxy, hydroxyl, $C_1$–$C_6$ alkanoyl, halogen, carboxyl, $C_2$–$C_6$ alkanoxy, nitro, sulfo, and sulfhydryl, or wherein two of $R_3$ are, together, an oxo group or a double bond between two adjacent X atoms; and
wherein Z is a nitrogen-protecting group and
(b) thereafter removing said nitrogen-protecting group, whereby said compound having the formula (I) is generated.

2. The method of claim 1, wherein said nitrogen-protecting group is selected from the group consisting of a 9-fluorenylmethoxy-carbonyl group, and a butoxycarbonyl group.

3. The method of claim 2, wherein said nitrogen-protecting group is a butoxycarbonyl group.

4. The method of claim 1, wherein said rhodium catalyst is a dirhodium (II) tetrakis[methyl 2-oxopyrrolidine-5(R)-carboxylate] catalyst.

5. The method of claim 1, wherein each X is carbon.

6. The method of claim 5, wherein p is 4.

7. The method of claim 6, wherein q is 8 and each $R_3$ is hydrogen.

8. The method of claim 1, wherein A is a phenyl group.

9. The method of claim 1, wherein n is 0.

10. The method of claim 9, wherein A is a phenyl group.

11. The method of claim 10, wherein m is 0.

12. The method of claim 1, wherein $R_2$ is methyl.

13. The method of claim 1, wherein said methylphenidate derivative is D-threo-methylphenidate.

14. The method of claim 13, wherein said first compound is methylphenyldiazoacetate.

15. The method of claim 14, wherein said second compound is N-butoxycarbonyl piperidine.

16. The method of claim 1, wherein the ratio of said methylphenidate derivative to the erythro-diastereomer thereof is greater than 1.00.

17. The method of claim 1, wherein the ratio of said methylphenidate derivative to the L-enantiomer thereof is greater than 1.00.

* * * * *

UNITED STATES PATENT AND TRADEMARK OFFICE
CERTIFICATE OF CORRECTION

PATENT NO. : 6,025,502
DATED : February 15, 2000
INVENTOR(S) : Winkler, et. al.

It is certified that error appears in the above-identified patent and that said Letters Patent is hereby corrected as shown below:

Title page, item [54], and col. 1, line 1,

In the Title, please delete "ENANTOPSELECTIVE" and substitute in place there of -- ENANTIOSELECTIVE --.

In the surname of the first-named inventor, please delete "Winklter" and substitute in place thereof -- Winkler --.

Signed and Sealed this

Fourteenth Day of November, 2000

Attest:

Q. TODD DICKINSON

*Attesting Officer*      *Director of Patents and Trademarks*